United States Patent
Maier et al.

(10) Patent No.: US 6,362,365 B1
(45) Date of Patent: Mar. 26, 2002

(54) PREPARATION OF TRIFLUOROBENZOIC ACIDS

(75) Inventors: Andreas Maier, Eppstein; Ralf Pfirmann, Griesheim, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/431,993

(22) Filed: Nov. 3, 1999

(30) Foreign Application Priority Data

Nov. 4, 1998 (DE) .......................................... 198 50 788

(51) Int. Cl.$^7$ ............................................... C07L 63/04

(52) U.S. Cl. .................... 562/493; 562/480; 558/411

(58) Field of Search ............................. 562/493, 480; 558/411

(56) References Cited

FOREIGN PATENT DOCUMENTS

| EP | 0 287 951 | 10/1988 |
|---|---|---|
| JP | 04074167 | 3/1992 |
| WO | WO 89/06649 | 7/1989 |

OTHER PUBLICATIONS

XP–002130612 Patent Abstract for JP 4074167.
H. Miyamoto et al., "Synthesis and Biological Properties of Substituted 1,4–Dihydro–5–methyl–4–oxo–3–quinolinecarboxylic Acids", Biorganic and Medicinal Chemistry, vol. 3, No. 12, pp. 1699–1706, 1995.
S.E. Hagen et al., "Synthesis of 5–Methyl–4–oxo–quinolinecarboxylic Acids", J. Heterocycl. Chem. 27 (1990) 1609–1616.
D.J. Milner, "The Mono–Alkyldecyanation of Tetrafluoroterephthalonitrile by Reaction With Grignard Reagents", J. Organometallic Chemistry; 302 (1986) 147–152.

*Primary Examiner*—Paul J. Killos
(74) *Attorney, Agent, or Firm*—Scott E. Hanf

(57) ABSTRACT

The present invention relates to a process for preparing trifluorobenzoic acids of the formula (1)

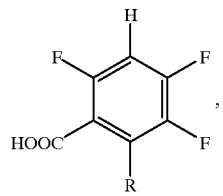

in which R is a straight-chain or branched alkyl radical having 1 to 6 C-atoms, an unsubstituted phenyl radical, a substituted phenyl radical which contains one or two alkyl or alkoxy groups having in each case 1 to 4 C atoms, or an araliphatic radical having 7 to 12 C atoms, which comprises reacting a compound of the formula (2)

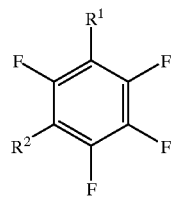

in which $R^1$ and $R^2$ are identical or different and are —CN, —COOR$^3$, where $R^3$ is H, Li, Na, K, MgCl, MgBr, MgI, ½Mg, ½Ca or an alkyl radical having 1 to 6 C atoms, or —CONR$^4$R$^5$, where $R^4$ and $R^5$ are identical or different and are an alkyl radical having 1 to 6 C atoms, with at least one organometallic compound of the formula CuR, CuLiR$_2$, MgXR, ZnR$_3$, LiR, AlX$_2$R, AlXR$_2$AlR$_3$ Al$_2$Cl$_3$R$_3$, where R is as defined in formula (1) and X is Cl, Br or I, in the presence of an inert solvent at from −80 to +150° C., treating the reaction product in the presence of water in the absence or presence of an acid at from 0 to 250° C. and decarboxylating the resulting trifluoroisophthalic acid of the formula (3)

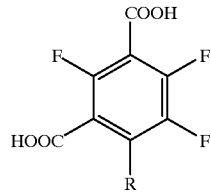

at from 80 to 280° C.

14 Claims, No Drawings

PREPARATION OF TRIFLUOROBENZOIC ACIDS

CROSS-REFERENCE TO RELATED APPLICATION

The present invention is described in the German priority application No. DE 19850788, filed Nov. 4, 1998, which is hereby incorporated by reference as is fully disclosed herein.

BACKGROUND OF THE INVENTION

The present invention relates to the preparation of trifluorobenzoic acids of the formula

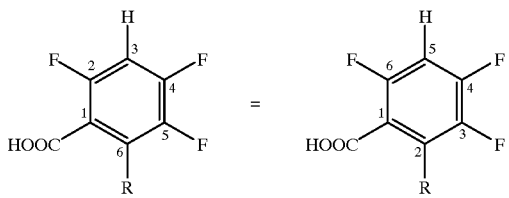

Such 2,4,5-trifluorobenzoic acids which are substituted in the 6-position by a radical R and which can also be referred to as 3,4,6-trifluorobenzoic acids which are substituted in the 2-position are interesting starting materials for preparing quinoline derivatives having antibacterial action. In Bioorganic & Medicinal Chemistry 3 (1995) 1699–1706, H. Miyamoto et al. describe the preparation of 5-methylquinolinecarboxylic acid derivatives which are highly active against gram-positive bacteria, starting from 3,4,6-trifluoro-2-methylbenzoic acid (=6-methyl-2,4,5-trifluorobenzoic acid). Compare also page 1699, left-hand column.

The preparation of the required 3,4,6-trifluoro-2-methylbenzoic acid (6-methyl-2,4,5 -trifluorobenzoic acid) is illustrated in simplified form by the reaction scheme below. Compare also p. 1700, preparation of compounds 1 to 4.

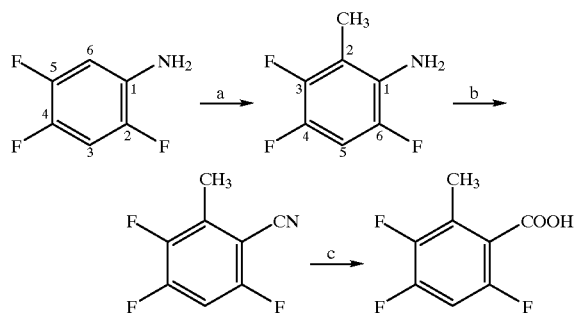

The preparation, which is characterized by a large number of individual steps and starts with 2,4,5-trifluoroaniline, is described on page 1703, left-hand column, in the examples relating to the preparation of 3,4,6-trifluoro-2-methylaniline, 3,4,6-trifluoro-2-methylbenzonitrile and 3,4,6-trifluoro-2-methylbenzoic acid (6-methyl-2,4,5-trifluorobenzoic acid).

This preparation has the disadvantages that, on the one hand, it requires a relatively large number of individual steps, inter alia, the use of dimethylsulfide in the preparation of 3,4,6-trifluoro-2-methylaniline, which is not without problems, and, on the other hand, that the 2,4,5-trifluoroaniline, which is used as starting material, is not easily obtainable and can only be obtained via a multi-step synthesis.

It is furthermore disadvantageous that the yield of 3,4,6-trifluoro-2-methylaniline is only 40%, that of 3,4,6-trifluoro-2-methylbenzonitrile is only 38% and that of 3,4,6-trifluoro-2-methylbenzoic acid (6-methyl-2,4,5-trifluorobenzoic acid) is 79%. This corresponds to an overall yield of only 12%, based on 2,4,5-trifluoroaniline. This very low overall yield is no incentive to realize this route of preparation industrially.

Another 4-step preparation which starts with 1-bromo-2,4,5-trifluorobenzene and which is represented in a simplified manner by the reaction scheme below, is described in J. Heterocycl. Chem. 27 (1990)1609–1616.

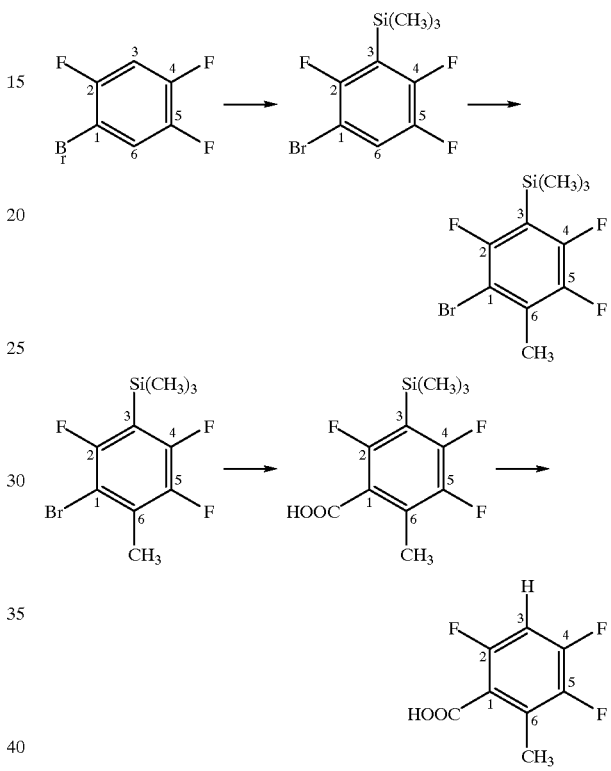

This preparation route is very expensive. The first and the second synthesis step each involve reaction with butyllithium and diisopropylamine in tetrahydrofuran at −78° C., and the third synthesis step involves reaction with butyllithium in ether, likewise at −78° C. In the first step, 1-bromo-2,4,5-trifluorobenzene is reacted first with lithium diisopropylamide and then with trimethylsilyl chloride, the resulting 1-bromo-2,4,5-trifluoro-3-(trimethylsilyl)benzene (88% yield) is once more reacted with lithium diisopropylamide and subsequently with methyl trifluoromethanesulfonate, the resulting 1-bromo-2,4,5-trifluoro-6-methyl-3-(trimethylsilyl)benzene (75% yield) is reacted with butyllithium and subsequently with $CO_2$ in the form of dry ice, and the resulting 2,4,5-trifluoro-6-methyl-3-(trimethylsilyl)- benzoic acid (62% yield) is reacted with cesium fluoride in acetonitrile to give 6-methyl-2,4,5-trifluorobenzoic acid (89% yield).

This synthesis route comprises many individual steps, makes use of some very expensive materials (for example methyl trifluoromethanesulfonate, cesium fluoride) and affords the end product in an overall yield of only 36.4%, based on 1-bromo-2,4,5-trifluorobenzene. Compare also the examples in J. Heterocycl. Chem. 27 (1990) page 1612, right-hand column, bottom, and page 1614, left-hand column.

SUMMARY OF THE INVENTION

With a view to the disadvantages described above, it is an object of the present invention to provide a process which avoids these disadvantages, which uses easily obtainable starting materials, which can be realized at reasonable expense and which affords the desired end product in an acceptable yield.

This object is achieved by a process for preparing trifluorobenzoic acids of the formula

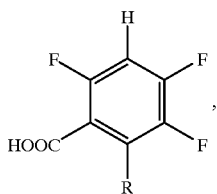

(1)

in which R is a straight-chain or branched alkyl radical having 1 to 6 C atoms, an unsubstituted phenyl radical, a substituted phenyl radical which contains one or two alkyl or alkoxy groups having in each case 1 to 4 C atoms, or an araliphatic radical having 7 to 12 carbon atoms.

It is characterized in that a compound of the formula

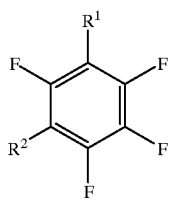

(2)

in which $R^1$ and $R^2$ are identical or different and are —CN, —COOR$^3$, where $R^3$ is H, Li, Na, K, MgCl, MgBr, MgI, ½Mg, ½Ca or an alkyl radical having 1 to 6 C atoms, or —CONR$^4$R$^5$, where $R^4$ and $R^5$ are identical or different and are an alkyl radical having 1 to 6 C atoms, is reacted with at least one organometallic compound of the formula CuR, CuLiR$_2$, MgXR, ZnR$_2$, LiR, AlX$_2$R, AlXR$_2$, AlR$_3$ or Al$_2$Cl$_3$R$_3$, where R is as defined in formula (1) and X is Cl, Br or I, in the presence of an inert solvent at from −80 to +150° C., the reaction product is treated in the presence of water in the absence or presence of an acid at from 0 to 250° C. and the resulting trifluoroisophthalic acid of the formula

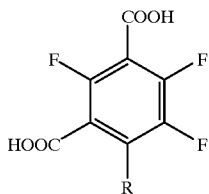

(3)

is decarboxylated at from 80 to 280° C.

The starting materials of formula (2) required for the process according to the invention can be prepared in a relatively simple manner and in good yields, starting from easily obtainable tetrachloroisophthalonitrile, which can easily be converted into the tetrafluoroisophthalonitrile by chlorine-fluorine exchange (reaction with KF), and, if required, by reacting the tetrafluoroisophthalonitrile by customary methods to give tetrafluoroisophthalic acid, salts of tetrafluoroisophthalic acid, tetrafluoroisophthalic esters and tetrafluoroisophthalamides.

DESCRIPTION OF THE PREFERRED EMBODIMENTS

The process according to the invention is based on a short reaction sequence of only three steps, namely 1. On the reaction of the compound of the formula (2) with the organometallic compound, 2. On the treatment of the resulting reaction product with the acid in the presence of water and 3. On the decarboxylation of the trifluoroisophthalic acid, giving the desired end product of the formula (1), i.e. the 2,4,5-trifluorobenzoic acid which is substituted in the 6-position.

In the reaction of carbonyl groups with organometallic compounds, for example in the reaction of nitriles or carboxylic esters with Grignard reagents, imines or amines and ketones or alcohols, respectively, are usually formed. It is surprising that these reactions do not occur in the process according to the invention.

An exchange of a nitrile group for an alkyl group of a Grignard reagent, as in the reaction of tetrafluoroterephthalonitrile with methylmagnesium bromide, where 4-methyl-2,3,5,6-tetrafluorobenzonitrile is formed (J. Organometallic Chem. 302 (1986), 147–152), does not take place. This was likewise not expected and is also to be considered as surprising.

A further advantage of the process according to the invention is that, in the first step of the synthesis, the exchange of fluorine in the 6-position for the radical R takes place with high selectivity, and other isomers originating from the exchange of other fluorine radicals are only formed in relatively low amounts.

Moreover, it is surprising that, in the last step of the synthesis, the decarboxylation of the 2,4,5-trifluoroisophthalic acid which is substituted in the 6-position proceeds with very high selectivity, affording the corresponding 2,4,5-trifluorobenzoic acid which is substituted in the 6-position.

With good results, a compound of the formula (2) in which $R^1$ and $R^2$ are identical or different and are —CN or —COOR$^3$, where $R^3$ is H, Li, Na, K, MgCl, MgBr, MgI, ½Mg, ½Ca or an alkyl radical having 1 to 6, preferably 1 to 4, carbon atoms, in particular Na, K, MgCl or MgBr, preferably Na, K or MgCl, can be used as starting material for the process.

In a number of cases, it has been found to be favorable to use a compound of the formula (2) in which the radicals $R^1$ and $R^2$ are identical and have the meaning given in formula (2), in particular in which the radicals are identical and are —CN, —COONa or —COOMgCl, preferably —COONa or —COOMgCl, as starting material.

It has been found to be advantageous to use a compound of the formula (2) in which the radicals $R^1$ and $R^2$ are identical and are —COOLi, —COOMgCl, —COOMgBr or —COOMgI, prepared by reaction of tetrafluoroisophthalic acid in an inert solvent with an organometallic compound LiR$^6$, MgClR$^6$, MgBrR$^6$ or MgIR$^6$, in which $R^6$ is a straight-chain or branched alkyl radical having 1 to 6 carbon atoms, an unsubstituted phenyl radical, a substituted phenyl radical which contains one or two alkyl or alkoxy groups with in each case 1 to 4 C atoms, or an araliphatic radical having 7 to 12 C atoms, as starting material.

The process can be conducted in a particularly advantageous manner by using a compound of the formula (2), in which $R^1$ and $R^2$ are identical and are —COOMgCl, —COOMgBr or —COOMgI, in particular —COOMgCl or —COOMgBr, preferably —COOMgCl, prepared by reaction of tetrafluoroisophthalic acid in an inert solvent with $MgClR^6$, $MgBrR^6$ or $MgIR^6$, in particular $MgClR^6$ or $MgBrR^6$, preferably $MgClR^6$, in which $R^6$ is an o-tolyl radical, as starting material.

The reaction of the tetrafluoroisophthalic acid, which corresponds to a compound of the formula (2), in which $R^1$ and $R^2$ are each —COOH, is generally carried out under the conditions which are used for the reaction of the compound (2) with the organometallic compound containing the radical R.

The tetrafluoroisophthalic acid is reacted with the organometallic compound which contains the radical $R^6$ at from −80 to +150° C., in particular from −70 to 100, preferably from 0 to 80° C. The inert solvent used can be one of the inert solvents described in more detail below. It is particularly simple to employ the same solvent which is used for reacting the compound (2) with the organometallic compound which contains the radical R.

As mentioned above, at least one organometallic compound of the formula CuR, $CuLiR_2$, MgXR, $ZnR_2$, LiR, $AlX_2$, $AlXR_2R_1$, $AlR_3$ or $Al_2Cl_3R_3$, in particular MgXR, LiR, $AlX_2R$, $AlXR_2$, $AlR_3$ or $Al_2Cl_3R_3$, preferably MgXR, LiR or $AlR_3$ is employed.

It is also possible to use mixtures of organometallic compounds, for example (CuR+CuLiR), (MgClR+MgBrR), (MgClR+MgIR), (MgClR+MgBrR+MgIR), ($AlX_2R$+$AlXR_2$), ($AlX_2R$+$AlR_3$) or ($AlXR_2$+$AlR_3$).

In many cases, it is sufficient to employ a single organometallic compound of the abovementioned type.

In the organometallic compound, the radical R is as defined in the compound (1). R is in particular a straight-chain or branched alkyl radical having 1 to 6, preferably 1 to 4, C atoms, an unsubstituted phenyl radical or a substituted phenyl radical which contains one or two alkyl or alkoxy groups, is preferably a straight-chain or branched alkyl radical having 1 to 6, preferably 1 to 4, C atoms or an unsubstituted phenyl radical and is particularly preferably a straight-chain or branched alkyl radical having 1 to 6, preferably 1 to 4, C atoms.

The reaction of the compound (2) with the organometallic compound is carried out in the presence of an inert solvent or solvent mixture, i.e. a solvent or solvent mixture which does not react under the reaction conditions.

The inert solvent used can be an aromatic hydrocarbon having 6 to 14, preferably 6 to 10, C atoms, a trialkylamine having 1 to 18, preferably 2 to 12, C atoms per alkyl radical, where the alkyl radical may contain alkoxy groups having 1 to 4 C atoms as substituents, an aliphatic ether having 1 to 6 C atoms per alkyl radical, a cycloaliphatic ether having 4 to 6 carbon atoms in the ring, an alkyl ether of polyhydric alcohols having 2 to 6 C atoms in the alcohol radical and 1 to 4 C atoms per alkyl radical, an alkyl ether of polyethylene glycol having 2 to 22, in particular 3 to 12, preferably 3 to 8, ethylene glycol units and 1 to 4, in particular 1 to 2, C atoms per alkyl radical, or a mixture of these solvents, in particular an aliphatic ether having 1 to 6, preferably 2 to 4, C atoms per alkyl radical, a cycloaliphatic ether having 4 to 6, preferably 4 to 5, C atoms in the ring, an alkyl ether of polyhydric alcohols having 2 to 6, preferably 2 to 4, C atoms in the alcohol radical and 1 to 4, preferably 1 to 2, C atoms per alkyl radical, an alkyl ether of polyethylene glycol having 2 to 22, in particular 3 to 12, preferably 3 to 8, ethylene glycol units and 1 to 4, in particular 1 to 2, C atoms per alkyl radical, or a mixture of these solvents.

Without the list being meant to be complete the following solvents may be mentioned as examples of the abovementioned inert solvents: toluene, ortho-xylene, meta-xylene, para-xylene, technical mixtures of isomeric xylenes, diphenylmethane, trialkylamines having 6 to 14 carbon atoms per alkyl radical, mixtures of these trialkylamines, for example having 8 to 10 carbon atoms per alkyl radical (Hostarex A 327, trade product of Hoechst AG), methyl tert-butyl ether, dimethoxyethane, tetrahydrofuran, dioxane, diisopropyl ether, PEG-dimethyl ether 250, tributylamine, diglyme, triglyme, in particular toluene, tetrahydrofuran, diglyme, triglyme. In many cases, toluene or tetrahydrofuran were found to be particularly suitable.

As already mentioned above, the reaction of the compound of the formula (2) with the organometallic compound is carried out at from −80 to +150, in particular from −70 to +100, preferably from −50 to +70° C. It has to be taken into account here that the temperature to be selected depends to a certain extent on the organometallic compounds used and the radicals $R^1$ and $R^2$ in the compound (2). Organometallic compounds which are very reactive in combination with activating radicals $R^1$ and $R^2$ require relatively low temperatures, for example from −80 to +50, in particular from −50 to +30° C., organometallic compounds of average reactivity require slightly higher temperatures, for example from −20 to +100, in particular from 0 to 80° C., whereas organometallic compounds of a relatively low reactivity are employed at relatively high temperatures, for example at from 50 to 150, in particular from 70 to 140° C.

LiR, MgXR and $CuLiR_2$ are very reactive, $ZnR_2$, $AlR_3$ and CuR have an average reactivity, whereas $AlX_2R$ and $AlXR_2$ can be assigned a relatively low reactivity.

Activating groups $R^1$, $R^2$ are —CN, —$COOR^3$ where $R^3$=alkyl, less activating groups are —$CONR^4R^5$; —$COOR^3$ where $R^3$=H, Li, Na, K, MgCl, MgBr, MgI, ½Mg or ½Ca have low reactivity combined with high selectivity.

The compound of the formula (2) is usually employed in the inert solvent in a concentration of from 1 to 1000, in particular from 10 to 500, preferably from 50 to 300, g per liter of inert solvent.

The organometallic compound and the compound of the formula (2) are usually employed in a molar ratio of (0.1 to 5):1, in particular of (0.2 to 2):1, preferably of (0.3 to 1.2):1, particularly preferably of (0.5 to 1.1):1.

In general, the organometallic compound is also employed in the form of a solution which usually comprises from 0.5 to 10, in particular from 1 to 5, preferably from 1.5 to 4, mol of organometallic compound per liter of inert solvent.

It is possible to initially charge all or some of the required amount of the compound (2) and then to add the organometallic compound with stirring at reaction temperature. It is also possible to add the compound (2) and the organometallic compound separately but simultaneously and to react them with stirring.

After the reaction has ended, stirring is continued for a short while, any organometallic compound that is still present is destroyed using water, the inert solvent is removed and the reaction product which is formed in the reaction of the compound of the formula (2) with the organometallic compound is treated in the presence of water in the absence or presence of an acid, in particular with an aqueous acid. The acid used can be a mineral acid or an aliphatic carboxylic acid having 1 to 4 carbon atoms, in particular a hydrohalic acid, phosphoric acid, nitric acid, sulfuric acid, acetic acid or a mixture, preferably sulfuric acid.

In a number of cases it may be advantageous to purify the reaction product by distillation before the acid treatment, and to recover unreacted starting material.

The treatment with acid is carried out at from 0 to 250° C.

If the reaction product contains —CN, —COOR$^3$ (R$^3$= alkyl) or —CONR$^4$R$^5$ radicals, the treatment with the acid is carried out at temperatures from 50 to 250° C., in particular from 100 to 200° C., preferably from 120 to 180° C., and these radicals are converted into the corresponding carboxylic acid.

If the reaction product contains —COOLi, —COONa, —COOK, —COOMgCl, —COOMgBr, —COOMgI, —COOMg/2 or —COOCa/2 radicals, a relatively low stoichiometric excess of acid of from 1 to 100, in particular from 5 to 20, preferably from 10 to 15, % at temperatures from 0 to 50° C., is usually sufficient to generate the —COOH group. High temperatures are not required here.

The reaction product which is formed by the reaction of the compound of the formula (2), in which R$^1$, R$^2$, are —CN, —CONR$^4$R$^5$, —COOR$^3$ (R$^3$=alkyl) with the organometallic compound is reacted with water, usually in a ratio by weight of from 100:1 to 0.5:1, in particular from 10:1 to 1:1, based on the compound of the formula (2). Here, the acid is usually employed in a ratio by weight of from 0.001:1 to 10:1, in particular from 0.01:1 to 5:1, preferably from 0.1:1 to 2:1, based on the water employed. The treatment with acid in the presence of water results in the hydrolytic formation of the trifluoroisophthalic acid of the formula

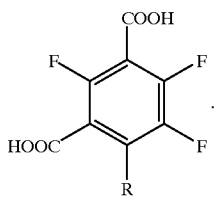

(3)

From the reaction mixture which comprises the trifluoroisophthalic acid of the formula (3), the trifluoroisophthalic acid is, if appropriate after dilution with water, obtained by extraction with a water-immiscible solvent.

Instead of using extraction, the reaction mixture which comprises the trifluoroisophthalic acid of the formula (3) can be concentrated by distillation in the absence or presence of a high-boiling solvent, the trifluoroisophthalic acid of the formula (3) can be filtered off and then decarboxylated, or the trifluoroisophthalic acid of the formula (3) can be decarboxylated in the presence of the high-boiling solvent.

The water-immiscible solvent used for extracting the trifluoroisophthalic acid can, for example, be one of the inert solvents or solvent mixtures listed above—as long as they are not water-miscible or water-soluble.

Examples of water-immiscible solvents which may be mentioned are dialkyl ether having 1 to 6, in particular 2 to 4, carbon atoms per alkyl radical, aromatic hydrocarbons having 6 to 12, in particular 6 to 9, carbon atoms, mono- or polychlorinated aromatic hydrocarbons having 6 to 12, in particular 6 to 9, carbon atoms, aliphatic hydrocarbons having 5 to 12 carbon atoms, mono- or polychlorinated aliphatic hydrocarbons having 1 to 8, in particular 1 to 6, carbon atoms, cycloaliphatic hydrocarbons having 5 to 12, in particular 6 to 9, carbon atoms, mono- or polychlorinated cycloaliphatic hydrocarbons having 5 to 12, in particular 6 to 9 carbon atoms, aliphatic ketones having 4 to 12, in particular 5 to 10, carbon atoms, esters of aliphatic carboxylic acids having 1 to 6 carbon atoms and aliphatic alcohols having 1 to 4 carbon atoms, or mixtures of these solvents, without this list being meant to be complete.

Examples of suitable water-immiscible solvents are diethyl ether, methyl tert-butyl ether, dibutyl ether, benzene, toluene, ortho-xylene, meta-xylene, para-xylene, mixtures of isomeric xylenes, chlorobenzene, dichlorobenzene, chlorotoluene, dichlorotoluene, hexane, dichloromethylene, chloroform, trichloroethane, cyclohexane, methyl ethyl ketone, diethyl ketone, methyl propyl ketone, methyl butyl ketone, di-n-butyl ketone, methyl acetate, ethyl acetate, propyl acetate, butyl acetate, methyl propionate, methyl butyrate or mixtures of these solvents.

If desired, the residue obtained after removal of the solvent can be recrystallized for purification. Solvents which are suitable for this purpose are, for example, water, aqueous acids, in particular aqueous mineral acids, acetic acid, aliphatic alcohols having 1 to 4 C atoms and aliphatic hydrocarbons having 5 to 12 C atoms.

Particularly suitable are water, aqueous acids and hexane.

The decarboxylation is carried out in the presence of an inert solvent or a base, in particular an N-containing organic compound, or in the presence of an inert solvent and a base, in particular an N-containing organic compound.

The decarboxylation of the trifluoroisophthalic acid of the formula (3) is usually carried out by heating in an inert solvent. Suitable for use as inert solvent are aliphatic hydrocarbons having 8 to 20 C atoms, aromatic hydrocarbons having 6 to 15 C atoms, chlorinated aliphatic hydrocarbons having 8 to 20 C atoms, chlorinated aromatic hydrocarbons having 6 to 15 C atoms, dialkylamides of an aliphatic carboxylic acid having 1 to 6 C atoms and dialkylamines having 1 to 4 carbon atoms, for example dimethylformamide, diethylformamide, dimethylacetamide, diethylacetamide, N-methylpyrrolidone, tetramethylurea, aliphatic sulfones, for example dimethyl sulfoxide or sulfolane, aliphatic or aromatic nitriles, for example acetonitrile or benzonitrile, aliphatic ethers having 4 to 10 C atoms per alkyl radical, alkyl ethers of polyhydric alcohols having 2 to 6, preferably 2 to 4, C atoms in the alcohol radical and 1 to 4, preferably 1 to 2, C atoms per alkyl radical, alkyl ethers of polyethylene glycol having 2 to 22, in particular 3 to 12, preferably 3 to 8, ethylene glycol units and 1 to 4, in particular 1 to 2, C atoms per alkyl radical, for example triglyme or PEG 250, aliphatic alcohols having 4 to 10 C atoms, aliphatic diols having 2 to 6 C atoms, for example ethylene glycol, aliphatic triols, for example glycerol. In a large number of cases, it was found to be advantageous to use, as inert solvent, sulfolane, dimethylformamide, dimethylacetamide or triglyme.

As already mentioned at the outset, the reaction temperature required for the decarboxylation is from 80 to 280° C. In many cases, a reaction temperature of from 100 to 270, in particular from 120 to 250, preferably from 120 to 230° C. was found to be sufficient for carrying out the decarboxylation.

The decarboxylation can be carried out in the presence of a water-soluble base or a water-insoluble organic base, in particular in the presence of a water-insoluble organic base.

Suitable organic bases are N-containing organic compounds, in particular water-insoluble amines.

The water-soluble or water-insoluble organic base, in particular the water-insoluble amine, can be employed in relatively small amounts, but also in relatively large amounts. In general, from 0.001 to 50, in particular from 0.01 to 2, preferably from 0.05 to 1, particularly preferably from 0.1 to 0.5, mol of the organic base, in particular the water-insoluble amine, are employed per mole of the trifluoroisophthalic acid of the formula (3). It is also possible to employ the organic base on its own, without addition of one of the abovementioned inert solvents. However, it is also possible to carry out the decarboxylation in the presence of both an inert solvent and a base.

The term water-insoluble amine is to be understood as meaning those amines which are either sparingly soluble in water or not soluble at all. In general, the water-insoluble amine used is an alkylamine having 6 to 30 carbon atoms, a dialkylamine having 6 to 30 carbon atoms per alkyl radical, a trialkylamine having 4 to 30 carbon atoms per alkyl radical, an N-containing heterocyclic compound or a mixture of the substances mentioned above, in particular an alkyl amine having 8 to 20 carbon atoms in the alkyl radical, a dialkylamine having 8 to 20 carbon atoms per alkyl radical, a trialkylamine having 6 to 20 carbon atoms per alkyl radical, a non-alkylated or alkylated quinoline or pyridine, for example collidine, lutidine or picoline or a mixture of the substances mentioned above, preferably a trialkylamine having 6 to 20, in particular 6 to 14, preferably 8 to 12, carbon atoms per alkyl radical, or a mixture of these trialkylamines.

Without the list meant to be complete, the following compounds may be mentioned as examples of suitable amines: n-hexylamine, isohexylamine, n-heptylamine, isoheptylamine, n-octylamine, isooctylamine, n-nonylamine, isononylamine, n-decylamine, isodecylamine, n-dodecylamine, isododecylamine, n-hexadecylamine, isohexadecylamine, di-n-hexylamine, diisohexylamine, di-n-heptylamine, diisoheptylamine, di-n-octylamine, diisooctylamine, di-n-nonylamine, diisononylamine, di-n-decylamine, diisodecylamine, di-n-dodecylamine, diisododecylamine, di-n-hexadecylamine, diisohexadecylamine, tri-n-hexylamine, triisohexylamine, tri-n-heptylamine, triisoheptylamine, tri-n-octylamine, triisoctylamine, tri-n-decylamine, triisodecylamine, tri-n-dodecylamine, triisododecylamine, trialkylamines having straight-chain and/or branched chains of from 6 to 14 carbon atoms, pyridine, α-picoline, β-picoline, γ-picolin, 2,4-dimethylpyridine (α,γ-lutidine), 2,6-di-tert-butylpyridine, 2,4,6-trimethylpyridine (collidine), triethylpyridine, quinoline, methylquinolines, ethylquinolines, mixed amines, such as butyldihexylamine, dioctyidecylamine, hexyldioctylamine, dihexyloctylamine, diheptyloctylamine, didecyloctylamine, didodecyloctylamine, didodecyidecylamine, didecyidodecylamine, dioctyidodecylamine, dinonyloctylamine, dinonyidecylamine, dinonyidodecylamine.

In general, it is also possible to employ any mixtures of the abovementioned water-insoluble amines, in particular mixtures of different alkyl-, dialkyl- and trialkylamines, preferably mixtures of different trialkylamines having from 6 to 14, in particular from 8 to 12, carbon atoms.

The decarboxylation can be carried out in the presence or absence of a customary decarboxylation catalyst. Suitable decarboxylation catalysts are copper, a copper(h) compound or a copper(II) compound, for example copper(I) oxide, copper(II) oxide, copper(I) sulfate, copper(II) sulfate, copper(I) chloride, copper(II) chloride, copper(I) fluoride, copper(u) fluoride, copper carbonate, copper(I) hydroxide, copper(II) hydroxide, preferably copper(I) oxide and copper (II) oxide. It is also possible to employ any mixtures of the abovementioned compounds.

The decarboxylation catalyst is usually employed in an amount of from 0.1 to 10, in particular from 0.5 to 3, mol %, based on the trifluoroisophthalic acid of the formula (3).

If a water-insoluble inert solvent is used, the mixture is, after the decarboxylation has ended, extracted with an aqueous base, for example aqueous sodium hydroxide solution or aqueous potassium hydroxide solution, giving a basic extract of the reaction product.

If a water-soluble inert solvent is used, the mixture is, after the decarboxylation has ended, acidified with aqueous acid, and the reaction product is then extracted using a water-insoluble solvent.

Using an aqueous base, the salt of the trifluorobenzoic acid of the formula (1) is reextracted from this extract, and subsequently separated off as basic extract. The basic extracts are acidified and the trifluorobenzoic acid of the formula (1), which is liberated by the acidification, is crystallized or extracted using a water-insoluble organic solvent. The trifluorobenzoic acid can be obtained from the organic phase by evaporating the solvent or by crystallization. If desired, the trifluorobenzoic acid can be purified further by recrystallization, for example from water or aqueous acid or hexane. In general, the trifluorobenzoic acid obtained is already highly pure, so that additional purification is not required.

The process can be carried out continuously or batchwise. It can be carried out at reduced pressure, atmospheric pressure or elevated pressure.

The present invention furthermore relates to the compounds 2,4,5-trifluoro-6-methylisophthalonitrile

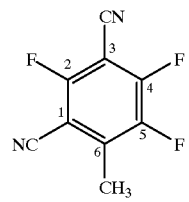

and 2,4,5-trifluoro-6-methylisophthalic acid

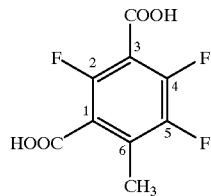

Both compounds open up an advantageous route for preparing 2,4,5-trifluoro-6-methylbenzoic acid, which for its part is an interesting starting material for preparing quinoline derivatives having antibacterial action.

The examples below describe the present invention in more detail, without restricting it thereto.

EXAMPLES

Experimental Part

Preparation of the Starting Materials

The experiments A and B below do not form part of the subject-matter of the present invention but serve to demonstrate the fact that the starting materials can be prepared in a simple manner.

Experiment A

Preparation of Tetrafluoroisophthalonitrile 200 g of tetrachloroisophthalonitrile, 250 g of potassium fluoride, 16 g of tetraphenylphosphonium bromide, 250 g of toluene are initially charged in 750 g of sulfolane, 245 g of distillate are then distilled off and the temperature is increased to 215° C. After 3 hours, the reaction mixture is cooled, and work-up by filtration and distillation of the reaction mixture gives: 112 g of tetrafluoroisophthalonitrile (b.p. 148–151° C. at 7 mbar, purity>98% according to GC).This corresponds to a yield of 75%.

M.p.: 77 to 78° C.

Experiment B

Preparation of Tetrafluoroisophthalic Acid

In 80 g of 70% strength sulfuric acid, 20 g of tetrafluoroisophthalonitrile are heated at 1600° C. for 30 min, and the mixture is then cooled, poured onto 240 g of ice and extracted with 80 g of methyl isobutyl ketone. The solvent is removed, leaving 22.8 g of tetrafluoroisophthalic acid (purity according to HPLC>99%). This corresponds to a yield of 95.7%.

M.p.: 216° C. (measured by DSC), lit.: 212 to 215° C.

The examples below serve to illustrate the process according to the invention:

Preparation of 2,4,5-trifluoro-6-methylisophthalonitrile

Example 1a

Excess of Methylmagnesium Bromide

In a 100 ml multi-necked flask, 5.04 g (25.2 mmol) of tetrafluoroisophthalonitrile, dissolved in 50 ml of tetrahydrofuran, are initially charged under protective gas and cooled to −50° C. At this temperature, 11.3 ml of a 3M solution of methylmagnesium bromide (34 mmol) are then added dropwise over a period of one hour. After an extra stirring time of 1 hour, at −50° C., the reaction mixture is poured into 20 ml of water and a pH of 1 is established using hydrochloric acid. The reaction mixture is extracted with dichloromethane and the solvent is removed. 6.3 g of a light-yellow oil remain as residue. GC analysis of this reaction product-shows the following composition:

<1% (GC-FID) of tetrafluoroisophthalonitrile 58.7% (GC-FID) of 2,4,5-trifluoro-6-methylisophthalonitrile (selectivity 58%, conversion>99%)

41.3% (GC-FID) of byproducts

According to HPLC (w/w), the reaction product contains: 43% by weight of 2,4,5-trifluoro-6-methylisophthalonitrile; this corresponds to a yield of 55%.

Example 1b

Substoichiometric Amounts of Methylmagnesium Bromide

The procedure of Example 1 is used, but 2 g (10 mmol) of tetrafluoroisophthalonitrile and 3 ml of methylmagnesium bromide solution (9 mmol) are employed, giving 2.1 g of a crude product of the following composition:

42.2% (GC-FID) of tetrafluoroisophthalonitrile 53.6% (GC-FID) of 2,4,5-trifluoro-6-methylisophthalonitrile (selectivity according to GC 93%, conversion 58%)

4.1% (GC-FID) of byproducts

Preparation of 2,4,5-trifluoro-6-methylbenzoic acid from tetrafluoroisophthalonitrile

Example 2 a) Preparation of 2,4,5-trifluoro-6-methylisophthalonitrile 250 g of tetrafluoroisophthalonitrile are dissolved in 2.5 l of tetrahydrofuran, and this mixture is initially charged at −50° C. At this temperature, 420 ml of a 3 M solution of methylmagnesium chloride are then added dropwise over a period of 8 hours. The reaction mixture is poured into water (5 l) and extracted with a total of 1 l of dichloromethane, giving, after removal of the solvent, 320.3 g of reaction product. Fractionation affords: 97.4 g of 2,4,5-trifluoro-6-methylisophthalonitrile (purity 97% according to GC) and 87 g of tetrafluoroisophthalonitrile (purity>98% according to GC), which were re-used for the subsequent batch. Using an analogous procedure, the subsequent batch gave 33.5 g of 2,4,5-trifluoro-6-methylisophthalonitrile (purity 97% according to GC FID) and 29.3 g of tetrafluoroisophthalonitrile which, when used again, affords 11 g of 2,4,5-trifluoro-6-methylisophthalonitrile.

Accordingly, the total yield of these three reactions is 137.7 g=56.2%, based on the tetrafluoroisophthalonitrile originally employed.

2,4,5-trifluoro-6-methylisophthalonitrile is characterized by the following data:

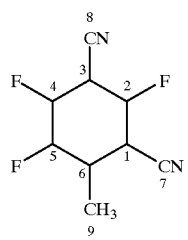

GC/MS: m/z=196

$^1$H NMR, 400.13 MHz, DMSO-d$_6$, (TMS)=0

| Signal | Multiplicity | ($^1$H) | Number of H | $J_{F,H}$ [Hz] | Assigned to |
|--------|--------------|---------|-------------|----------------|-------------|
| a | d | 2.56 | 3 | $J_{5\text{-}F,H}$ 2.6 | CH$_3$ |

| $^{13}$C NMR, 100.61 MHZ, DMSO-d$_6$, (DMSO-d$_6$) = 39.5 | | | | | |
|---|---|---|---|---|---|
| Signal | Multi-plicity$^1$ | ($^{13}$C) | Number of C | $J_{F,C}$ [Hz] | Assigned to |
| A | s | 159.48 | 1 | $^1J_{2\text{-}F,C}$ = 264.8, 4.3, 3.2 | C-2 |
| B | s | 153.05 | 1 | $^1J_{4\text{-}F,C}$ = 267.8, $^2J_{5\text{-}F,C}$ = 17.0, 5.7 | C-4 |

-continued

$^{13}$C NMR, 100.61 MHZ, DMSO-d$_6$, (DMSO-d$_6$) = 39.5

| Signal | Multi-plicity[1] | δ($^{13}$C) | Number of C | $J_{F,C}$ [Hz] | Assigned to |
|---|---|---|---|---|---|
| C | s | 145.01 | 1 | $^1J_{5-F,C}$ = 245.8, $^2J_{4-F,C}$ = 11.4, 3.9 | C-5 |
| D | s | 138.58 | 1 | $^2J_{5-F,C}$ = 18.1, 2.9, 1.7 | C-6 |
| E | s | 110.50 | 1 | 2.9, 2.2 | C-7 or C-8 |
| F | s | 107.63 | 1 | 3.3 | C-7 or C-8 |
| G | s | 99.73 | 1 | $^2J_{2-F,C}$ = 15.5, 5.0, 3.2 | C-1 |
| H | s | 92.19 | 1 | $^2J_{F,C}$ = 19.8, $^2J_{F,C}$ = 16.8, 2.1 | C-3 |
| I | q | 14.09 | 1 | 2.7, 2.7, 1.8 | CH$_3$ |

$^{19}$F NMR, 376.50 MHZ, DMSO-d$_6$, [CFCl$_3$ (virt. int.)] = 0

| Signal | Multi-plicity[2] | δ($^{19}$F) | Number of F | $J_{F,F}$[Hz] | $^1J_{F,C}$[Hz][3] | Assigned to |
|---|---|---|---|---|---|---|
| α | d | −104.2 | 1 | $^5J_{2-F,5-F}$ = 13.8 | 264.9 | 2-F |
| β | d | −119.4 | 1 | $^3J_{4-F,5-F}$ = 21.8 | 267.9 | 4-F |
| γ | dd | −139.2 | 1 |  | 245.9 | 5-F |

[1] without taking the peak splits caused by $J_{F,C}$ into account
[2] based on $^{19}$F {$^1$H}
[3] from the $^{13}$C-Satellites b) Preparation of 2,4,5-trifluoro-6-methylbenzoic acid 3.0 g of the 2,4,5-trifluoro-6-methylisophthalonitrile prepared above in 20 ml of 70% of sulfuric acid are heated at 130° C. for 24 hours. After cooling, the reaction mixture is poured into 80 ml of ice-water and extracted with methyl isobutyl ketone. The solvent is removed giving a yellow solid (3.4 g), having a purity, according to HPLC, of >95% and is identical to the reaction product described in Example 3.

Without further purification, this solid, together with 10 g of Hostarex A 327 (mixture of trialkylamines having 8 to 10 C atoms per alkyl radical; commercial product from Hoechst AG) was heated at 150° C. for 2 hours, work-up being carried out analogously to Example 4. This gives 2.4 g of 2,4,5-trifluoro-6-methylbenzoic acid (purity according to HPLC 97%), corresponding to a yield of 82%, based on the 2,5,6-trifluoro-4-methylisophthalonitrile employed, and 46%, based on the tetrafluoroisophthalonitrile employed.

Preparation of 2,4,5-trifluoro-6-methylisophthalic Acid from tetrafluoroisophthalic Acid Example 3

Under protective gas, 4 g of tetrafluoroisophthalic acid are initially charged in 50 ml of tetrahydrofuran at 20° C., and 11.2 ml of a 3 molar solution of methylmagnesium chloride are then added dropwise over a period of 1 hour to form the chloromagnesium salt of tetrafluoroisophthalic acid.

At from 20 to 30° C., another 5.7 ml of a 3 molar solution of methylmagnesium chloride are added to the resulting suspension. After the addition has ended, stirring is continued for another 1 hour and the mixture is then hydrolyzed with 100 g of water and acidified with hydrochloric acid. Extraction with methyl isobutyl ketone and removal of the solvent affords 3.8 g of a reaction product which, according to NMR spectroscopy, contains 85% of 2,4,5-trifluoro-6-methylisophthalic acid and 11% of unreacted tetrafluoroisophthalic acid. Accordingly, the selectivity is 95% and the yield is 82%. The purity of the crude product is 79% by HPLC. Purification is carried out by crystallization from dilute hydrochloric acid.

2,4,5-trifluoro-6-methylisophthalic acid is characterized by the following data:

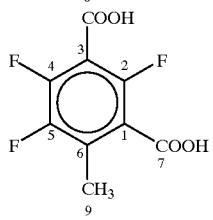

M.p.: 254° C. (from dilute hydrochloric acid, measured by DSC)

$^1$H NMR, 400.13 MHz, DMSO-d$_6$, δ(DMSO-d$_6$) = 2.50

| Signal | Multiplicity | δ ($^1$H) | Number of H | $J_{F,H}$ [Hz] | Assigned to |
|---|---|---|---|---|---|
| a | br. s | 14,02 | 2 |  | OH |
| b | d | 2,31 | 3 | $J_{5-F,H}$ = 2,4 | CH$_3$ |

$^{13}$C NMR, 100.61 MHz, DMSO-d$_6$, δ(DMSO-d$_6$) = 39.5

| Signal | Multi-plicity[4] | δ ($^{13}$C) | Number of C | $J_{F,C}$ [Hz] | Assigned to |
|---|---|---|---|---|---|
| A | s | 164.17 | 1 | $J_{F,C}$ = 2.1, 0.8 | C-7 or C-8 |
| B | s | 160.76 | 1 | $J_{F,C}$ = 2.4, > 1.1, > 0.5 | C-8 or C-7 |
| C | s | 151.50 | 1 | $^1J_{F,C}$ = 252.7, $J_{F,C}$ = 6.3, 3.2 | C-2 |
| D | s | 147.74 | 1 | $^1J_{4-F,C}$ = 256.8, $^2J_{5-F,C}$ = 16.1, $^3J_{2-F,C}$ = 8.2 | C-4 |
| E | s | 145.04 | 1 | $^1J_{5-F,C}$ = 243.2, $^2J_{4-F,C}$ = 12.9, $^4J_{2-F,C}$ = 3.7 | C-5 |
| F | s | 128.30 | 1 | $^2J_{F,C}$ = 16.6, $J_{F,C}$ = 4.8, 1.4 | C-6? |
| G | s | 120.35 | 1 | $^2J_{F,C}$ = 19.7, $J_{F,C}$ = 4.1, 2.2 | C-1? |
| H | s | 111.31 | 1 | $^2J_{F,C}$ = 22.1, 16.2 | C-3 |
| I | q | 11.95 | 1 | >1.9 | CH$_3$ |

[4] without taking the peak splits caused by $J_{F,C}$ into account

$^{19}$F NMR, 376.50 MHZ, DMSO-d$_6$, δ[CFCl$_3$ (virt. int.)] = 0

| Signal | Multi-plicity[5] | δ ($^{19}$F) | Number of F | $J_{F,F}$[Hz] | $^1J_{F,C}$ [Hz][6] | Assigned to |
|---|---|---|---|---|---|---|
| α | dd | −118.4 | 1 | $^5J_{2-F,5-F}$ = 15.2, $^4J_{2-F,4-F}$ = 1.3 | 252.8 | 2-F |
| β | dd | −133.6 | 1 | $^3J_{4-F,5-F}$ = 22.3 | 257.3 | 4-F |
| γ | dd | −142.9 | 1 |  | 243.0 | 5-F |

[5] based on $^{19}$F {$^1$H}
[6] from the $^{13}$C-Satellites

Preparation of 2,4,5-trifluoro-6-methylbenzoic Acid from Tetrafluoroisophthalic Acid

Example 4

20 g of tetrafluoroisophthalic acid are initially charged in 250 ml of THF and, at from 20 to 40° C., admixed with 88 ml of a 3 molar methylmagnesium chloride solution. Customary aqueous work-up (see Example 3) gives 20.1 g of 2,4,5-trifluoro-6-methylisophthalic acid. The purity of the product is 85% by HPLC.

Without further purification, 20 g of this crude product are suspended in 80 g of Hostarex A 327 and heated at 150° C. for 2 hours. After cooling, the mixture is extracted alkaline with 80 g of water and 8 g of 50% strength aqueous sodium hydroxide solution, the aqueous product phase is acidified using hydrochloric acid and the resulting precipitate is filtered off. This gives 14.8 g of filter cake. Drying at 50° C. gives 13.8 g of 2,4,5-trifluoro-6-methylbenzoic acid (purity according to HPLC 90%). Crystallization of this crude product from water gives 11.4 g of 2,4,5-trifluoro-6-methylbenzoic acid, purity according to HPLC 99.5%, which corresponds to a yield of 71%, based on the tetrafluoroisophthalic acid employed.

2,4,5-trifluoro-6-methylbenzoic acid is characterized by the following data:

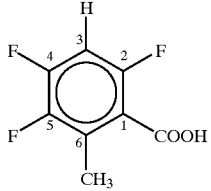

M.p.: 121° C. (from water, measured using DSC) lit.: 116 to 117° C.

| $^1$H NMR, 400.13 MHz, DMSO-$d_6$, $\delta$(TMS) = 0 | | | | |
|---|---|---|---|---|
| Signal | Multiplicity | $\delta$ ($^1$H) | Number of H | $J_{F,H}$ [Hz] | Assigned to |
| a | "dt" | 7.47 | 1 | $^3J_{4-F,H}{}^7$ = 10.6, $^3J_{2-F,H}{}^7$ = 9.5, $^4J_{5-F,H}$ = 3.6? | 3-H |
| b | d | 2.32 | 3 | $J_{5-F,H}$ = 2.6 | $CH_3$ |

[7]from the $^1$H coupled $^{19}$F NMR spectrum

| $^{13}$C NMR, 100.61 MHz, DMSO-$d_6$, $\delta$(DMSO-$d_6$) = 39.5 | | | | |
|---|---|---|---|---|
| Signal | Multiplicity[8] | $\delta$ ($^{13}$C) | Number of C | $J_{F,C}$ [Hz] | Assigned to |
| A | s | 164.64 | 1 | >2.1, 0.8 | COOH |
| B | s | 154.23 | 1 | $^1J_{F,C}$ = 247.0, 11.6, 3.1 | C-2 |
| C | s | 149.97 | 1 | $^1J_{F,C}$ = 250.7, 15.1, 14.0 | C-4 |
| D | s | 144.89 | 1 | $^1J_{F,C}$ = 241.1, $^2J_{F,C}$ = 12.6, 3.8 | C-5 |
| E | s | 126.33 | 1 | $^2J_{F,C}$ = 16.5, 4.6, 1.2 | C-6? |
| F | s | 119.79 | 1 | $^2J_{F,C}$ = 18.9, 4.0, 2.2 | C-1? |
| G | d | 103.89 | 1 | $^2J_{F,C}$ = 28.7 and 21.7 | C-3 |
| H | q | 11.71 | 1 | 4.2, 2.5, 1.8 | $CH_3$ |

[8]without taking the peak splits caused by $J_{F,C}$ into account

| $^{19}$F NMR, 376.50 MHz, DMSO-$d_6$, $\delta$[CFCl$_3$ (virt. int.)] =0 | | | | | |
|---|---|---|---|---|---|
| Signal | Multiplicity[9] | $\delta$ ($^{19}$F) | Number of F | $J_{F,F}$ [Hz] | $^1J_{F,C}$ | Assigned to |
| $\alpha$ | dd | −116.0 | 1 | $^5J_{2-F,5-F}$ = 15.0, $^4J_{2-F,4-F}$ = 5.0 | 246.9 | 2-F |
| $\beta$ | dd | −131.9 | 1 | $^3J_{4-F,5-F}$ = 22.3 | 250.5 | 4-F |
| $\gamma$ | dd | −144.9 | 1 | | 241.1 | 5-F |

[9]based on $^{19}$F {$^1$H}
[10]from the $^{13}$C-Satellites

Preparation of 2,4,5-trifluoro-6-methylbenzoic acid from tetrafluoroisophthalic acid

Example 4A

Under protective gas, 36 g of tetrafluoroisophthalic acid are initially charged in 500 ml of tetrahydrofuran at 20° C. 160 ml of a 1.7 molar solution of ortho-tolylmagnesium chloride in THF are then added dropwise and the mixture is stirred for another 1 hour to form the chloromagnesium salt of tetrafluoroisophthalic acid.

76 ml of a 3 molar solution of methylmagnesium chloride in THF are then metered in over a period of 2 hours, and stirring is continued for 30 min.

Work-up as in Example 3 gives 40.4 g of crude product with a purity of 73% according to HPLC.

Analogously to Example 4, 40 g of this crude product are introduced without further purification into Hostarex A 327, and the mixture is heated at 1 50oC for 2 hours. Work-up gives 44 g of crude product (purity according to HPLC 87%) which, by redissolution in water, gives 16.5 g of 2,4,5-trifluoro-6-methylbenzoic acid (yield 57.5%, based on the tetrafluoroisophthalic acid employed).

Preparation of 2,4,5-trifluoro-6-methylbenzoic acid by decarboxylation of 5-trifluoro-6-methylisophthalic acid

Examples 5 to 8

Preliminary experiments with respect to the solvents which can be employed

In each case 0.5 g of 6-methyl-2,4,5-trifluoroisophthalic acid are heated in 5 g of solvent, and the conversion into 2,4,5-trifluoro-6-methylbenzoic acid is determined by HPLC. The results are summarized in the table below:

| Example | Solvent | Temperature | Time | Conversion according to HPLC (a/a) |
|---|---|---|---|---|
| 5 | sulfolane | 200° C. | 8 h | 38% |
| 6 | sulfolane | 220° C. | 4 h | 99% |
| 7 | triglyme | 215° C. | 6 h | 99% |
| 8 | Hostarex A327 | 150° C. | 2 h | 99% |

Hostarex A 327 is a mixture of trialkylamines having 8 to 10 C atoms per alkyl radical.

Example 9

Preparative Reaction in Sulfolane

20° C., 18 g of 2,4,5-trifluoro-6-methylisophthalic acid (90% pure) are heated in sulfolane for 5 hours. After cooling and the addition of 400 g of water, the mixture is acedified using concentrated hydrochloric acid and then extracted with 80 g of toluene. The toluene extract is admixed with 50 g of water and made alkaline using aqueous sodium hydroxide solution, and the phases are separated. The product (16.1 g) is liberated from the aqueous phase by acidification. It is obtained as a solidifying oil which is separated off at 50° C. and has a purity of 89% according to HPLC. According to examination by NMR spectroscopy, this product still contains 6 mol % of sulfolane.

What is claimed is:

1. A process for preparing trifluorobenzoic acids of the formula

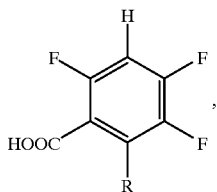

(1)

in which R is a straight-chain or branched alkyl radical having 1 to 6 C-atoms, an unsubstituted phenyl radical, a substituted phenyl radical which contains one or two alkyl or alkoxy groups having in each case 1 to 4 C atoms, or an araliphatic radical having 7 to 12 C atoms, which comprises reacting a compound of the formula

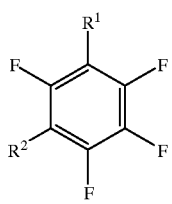

(2)

in which $R^1$ and $R^2$ are identical or different and are —CN, —COOR, where $R^3$ is H, Li, Na, K, MgCl, MgBr, MgI, ½Mg, ½Ca or an alkyl radical having 1 to 6 C atoms, or —CONR$^4$R$^5$, where $R^4$ and $R^5$ are identical or different and are an alkyl radical having 1 to 6 C atoms, with at least one organometallic compound of the formula CuR, CuLiR$_2$, MgXR, Zn R$_2$, LiR, AlX$_2$R, AlXR$_2$, AlR$_3$ or Al$_2$Cl$_3$R$_3$, where R is as defined in formula (1) and X is Cl, Br or I, in the presence of an inert solvent at from −80 to +150° C., treating the reaction product in the presence of water in the absence or presence of an acid at from 0 to 250° C. and decarboxylating the resulting trifluoroisophthalic acid of the formula

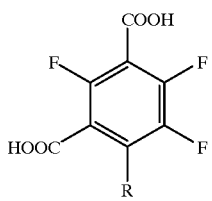

(3)

at from 80 to 280° C.

2. The process as claimed in claim 1, wherein a compound of the formula (2) in which $R^1$ and $R^2$ are identical or different and are —CN or —COOR$^3$, where $R^3$ is Na, K, MgCl or MgBr, is used.

3. The process as claimed in claim 1, wherein a compound of the formula (2) in which $R^1$ and $R^2$ are identical and are —CN—CN, —COONa—COONa or —COOMgCl is used as starting material.

4. The process as claimed in claim 1, wherein a compound of the formula (2) in which $R^1$ and $R^2$ are identical and are —COOLi, —COOMgCl, —COOMgBr or —COOMgI, prepared by reaction of tetrafluoroisophthalic acid in an inert solvent with an organometallic compound LiR$^6$, MgClR$^6$ or MgIR$^6$, in which $R^6$ is a straight-chain or branched alkyl radical having 1 to 6 carbon atoms, an unsubstituted phenyl radical, a substituted phenyl radical which contains one or two alkyl or alkoxy groups having in each case 1 to 4 C atoms, or an araliphatic radical having 7 to 12 C atoms, is used as starting material.

5. The process as claimed in claim 1, wherein a compound of the formula (2) in which $R^1$ and $R^2$ are identical and are —COOMgCl, —COOMgBr or —COOMgI, prepared by reaction of tetrafluoroisophthalic acid in an inert solvent with an organometallic compound MgClR$^6$, MgBrR$^6$ or MgIR$^8$, in which $R^6$ is an o-tolyl radical, is used as starting material.

6. The process as claimed in claim 1, wherein an organometallic compound of the formula MgXR, LiR, AlX$_2$R, AlXR$_2$, AlR$_3$ or Al$_2$Cl$_3$R$_3$ is used.

7. The process as claimed in claim 1, wherein an organometallic compound of the formula MgXR, LiR or AlR$_3$ is used.

8. The process as claimed in claim 1, wherein, as an inert solvent, an aromatic hydrocarbon having 6 to 14 C atoms, a trialkylamine having 1 to 18 C atoms per alkyl radical, where the alkyl radical may contain alkoxy groups having 1 to 4 C atoms as substituents, an aliphatic ether having 1 to 6 C atoms per alkyl radical, a cycloaliphatic ether having 4 to 6 carbon atoms in the ring, an alkyl ether of polyhydric alcohols having 2 to 6 C atoms in the alcohol radical and 1 to 4 C atoms per alkyl radical, an alkyl ether of polyethylene glycol having 2 to 22 ethylene glycol units and 1 to 4 C atoms per alkyl radical or a mixture of these solvents is used.

9. The process as claimed in claim 1, wherein, as inert solvent, an aliphatic ether having 1 to 6 C atoms per alkyl radical, a cycloaliphatic ether having 4 to 6 C atoms in the ring, an alkyl ether of polyhydric alcohols having 2 to 6 C atoms in the alcohol radical and 1 to 4 C atoms per alkyl radical or a mixture of these solvents is used.

10. The process as claimed in claim 1, wherein the reaction is carried out at from −70 to +100° C.

11. The process as claimed in claim 1, wherein the acid used to treat the reaction product is a mineral acid or an aliphatic arboxylic acid having 1 to 4 carbon atoms.

12. The process as claimed in claim 1, wherein the acid used to treat the reaction product is sulfuric acid.

13. The process as claimed in claim 1, wherein the decarboxylation is carried out in the presence of an inert solvent or a base or in the presence of an inert solvent and a base.

14. The compounds 2,4,5-trifluoro-6-methylisophthalonitrile and 2,4,5-trifluro-6-methylisophthalic acid.

* * * * *